United States Patent

Lerg et al.

[11] Patent Number: 6,132,738
[45] Date of Patent: Oct. 17, 2000

[54] SHOWER PREPARATIONS HAVING A HIGH OIL CONTENT

[75] Inventors: Heike Lerg; Bozena Gerber; Robert Schmucker; Otto Stelling, all of Hamburg, Germany

[73] Assignee: Beiersdorf Aktiengesellschaft, Hamburg, Germany

[21] Appl. No.: 09/046,911

[22] Filed: Mar. 24, 1998

[30] Foreign Application Priority Data

Mar. 26, 1997 [DE] Germany .............. 197 12 678

[51] Int. Cl.[7] .............. A61K 6/00; A61K 7/00; A61K 9/127; A61K 7/06
[52] U.S. Cl. .............. 424/401; 424/70.1; 424/450; 514/844; 514/846
[58] Field of Search .............. 424/401, 70.1, 424/450; 514/844, 846

[56] References Cited

U.S. PATENT DOCUMENTS

| 3,723,360 | 3/1973 | Hewitt | 252/542 |
| 5,653,988 | 8/1997 | Gerber et al. | 424/401 |

FOREIGN PATENT DOCUMENTS

| 0 026 073 A | 4/1981 | European Pat. Off. . |
| 0 026 73 A | 4/1981 | European Pat. Off. . |
| 0 47 916 A | 3/1982 | European Pat. Off. . |
| 0 691 127 | 1/1996 | European Pat. Off. . |
| 23 60 073 A | 6/1975 | Germany . |
| 29 43 202 A | 3/1981 | Germany . |
| 2 280 906 A | 2/1995 | United Kingdom . |

Primary Examiner—Thurman K. Page
Assistant Examiner—Todd D Ware
Attorney, Agent, or Firm—Norris, McLaughlin & Marcus, P.A.

[57] ABSTRACT

Cosmetic or dermatological shower preparations, characterized by (a) a content of at most 55% by weight, based on the total weight of the preparations, of one or more surfactants selected from the group consisting of trialkyl- and/or trialkanolamine salts of fatty alcohol sulphates and fatty alcohol ether sulphates and (b) a content of from 30 to 45% by weight, based on the total weight of the preparations, of one or more oil components selected from the group consisting of lipids, which contain from one to three acyl radicals, which have been esterified using an alcohol, (c) a water content of at most 3.5% by weight, based on the total weight of the preparation, (d) optionally containing one or more emulsifiers, (e) optionally containing further surfactants, and (f) optionally containing further cosmetic or pharmaceutical auxiliaries, additives and/or active substances.

10 Claims, No Drawings

SHOWER PREPARATIONS HAVING A HIGH OIL CONTENT

DESCRIPTION

Shower preparations having a high oil content

The present invention relates to cosmetic cleansing preparations containing trialkyl- and/or trialkanolamine salts of fatty alcohol sulphates and/or fatty alcohol ether sulphates, preferably for use as shower preparations.

Even cleansing the skin using a simple bath of water without added surfactants will initially cause the horny layer of the skin to swell. The degree of this swelling depends inter alia on the bathing time and the temperature of the water. Not only are water-soluble substances, e.g. water-soluble constituents of dirt, washed off, but endogenous substances of the skin, which are responsible for the water-binding ability of the horny layer, are also washed away. In addition, endogenous surface-active substances of the skin also cause fats in the skin to be dissolved to a certain extent and washed away. After the initial swelling, this subsequently causes the skin to dry out, which can be further intensified by detersive additives.

In healthy skin, these processes are generally of no consequence since the protective mechanisms of the skin can readily compensate for such slight disturbances to the upper layers of the skin. However, even in the case of non-pathological deviations from the norm, e.g. as a result of damage or irritation caused by the environment, light damage, ageing skin etc., the protective mechanism of the surface of the skin is disturbed. In some circumstances, it is then no longer able to fulfill its role by itself and must be regenerated using external measures. There has thus been no lack of attempts to find suitable cleansing preparation for the simultaneous regeneration of the skin.

Known products for cleansing and also caring for the skin are, for example, bath preparations, in particular bath oil preparations or oil cream bath preparations. Their functionality is generally limited to refatting or superfatting the upper most layers of the skin. The prior art describes, inter alia, bath oil preparations of a different type, it being possible to vary the properties of the fat or oil phase by adding surface-active substances. Depending on the type and quantity of the chosen constituents, it is possible to formulate preparations which produce spreading oily films, oil-in-water systems or also completely solubilized systems on the surface of the bath water. Foaming, but also low-foam or non-foaming formulations are possible.

DE-A 29 43 202 describes agents which have a cleansing and skin care effect and are based on mixtures of surfactants and oils, which are preferably used as soothing foam baths, and the use of these agents as shower preparations is of course also mentioned. The described preparations contain from 20 to 80% by weight of an aqueous surfactant solution, which for its part consists of from 85 to 95% by weight of surfactant and from 5 to 15% by weight of water, and has an oil content of from 80 to 20% by weight. The detersive component of these preparations consists of mono- or dialkylamine, mono- or dialkanolamine or alkylalkanolamine salts of fatty alcohol sulphuric acid esters.

U.S. Pat. No. 4,371,548 describes bath preparations and shower gels. These contain from 20 to 70% by weight of a surfactant mixture and have an oil content of from 20 to 60% by weight. The surfactant mixture in turn comprises from 10 to 90% by weight of one or more amines of $C_8$–$C_{18}$- fatty alcohol sulphates, which are optionally ethoxylated, and from 90 to 10% by weight of a metal ammonium $C_8$–$C_{18}$- fatty alcohol ether sulphate.

A significant disadvantage of bath preparations is that they are present in very dilute form since a bath tub can in some circumstances hold up to several hundred liters of water. This must be allowed for by formulating the preparation carefully or by employing large amounts of the oil bath preparation to be used.

Surfactant-containing shower preparations do not generally display any appreciable care action since they only have a low oil content. Using an oil bath preparation as a shower preparation, and therefore for a purpose for which it is not intended, is thus not an option. This use is inappropriate since such preparations produce a negligible amount of foam.

On the other hand, a relatively new development relates to surfactant-containing shower preparations having a high oil content. In this connection, DE-A 44 24 210 describes cosmetic or dermatological shower preparations having a surfactant content of at most 55% by weight and an oil content of more than 45% by weight, the preparations being essentially nonaqueous. In view of their high oil content, these preparations have a regenerating effect as regards the general condition of the skin. They also have good foam formation and high cleansing power.

It was surprising, and unforeseeable by the person skilled in the art, that shower preparations which have a markedly lower oil content are able to refat the skin to the same extent, having the advantage over the prior art of being higher foaming and better tolerated.

The present invention thus relates to cosmetic or dermatological shower preparations characterized by
(a) a content of at most 55% by weight, based on the total weight of the preparations, of one or more surfactants selected from the group consisting of trialkyl- and/or trialkanolamine salts of fatty alcohol sulphates and fatty alcohol ether sulphates and
(b) a content of from 30 to 45% by weight, based on the total weight of the preparations, of one or more oil components selected from the group consisting of lipids, which contain from one to three acyl radicals, which have been esterified using an alcohol,
(c) a water content of at most 3.5% by weight, based on the total weight of the preparation,
(d) optionally containing one or more emulsifiers,
(e) optionally containing further surfactants, and
(f) optionally containing further cosmetic or pharmaceutical auxiliaries, additives and/or active substances.

The preparations according to the invention have a very good foam formation, high cleansing power and a high skin care action. In particular, the preparations according to the invention have a skin-smoothing action, reduce the feeling of dryness in the skin and make the skin supple.

The fatty alcohol sulphates and fatty alcohol ether sulphates which are used favourably according to the invention advantageously have the following structure:

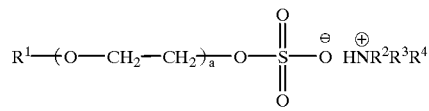

a is from 0 to 10, advantageously from 1 to 5, and $R^1$ is selected from the group consisting of branched and unbranched alkyl groups having from 6 to 24 carbon atoms, and $R^2$, $R^3$ and $R^4$, independently of one another, are selected from the group consisting of branched and unbranched alkyl and hydroxy alkyl radicals having from 1 to 24 carbon atoms.

Depending on the preparation it is possible that the surfactants used contain residual amounts of physiologically acceptable unreacted starting materials, for example 1,2-propylene glycol.

A preferred fatty alcohol ether sulphate is TIPA laureth sulphate.

The oils according to the invention are advantageously chosen from the group consisting of lipids. In the biochemical field, the term "lipids" covers certain biomolecules with a variety of structures. In the original sense, "lipids" are taken to mean fats, i.e. carboxylic acid esters of glycerol.

In the wider sense, this term is taken to mean a group of water-insoluble molecules which are characterized by at least one distinctly hydrophilic region of the molecule and at least one distinctly lipophilic region of the molecule. The phosphoric acid esters of acylated glycerols, the "phospholipids", and other compounds belong to this overall very inhomogeneous group of chemical compounds.

The most important phosphatidylcholines are, for example, the lecithins, which are characterized by the general structure

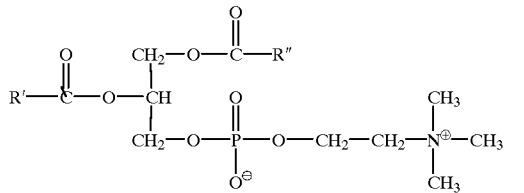

in which R' and R'' are typically unbranched aliphatic radicals having 15 or 17 carbon atoms and up to 4 cis double bonds.

The oils according to the invention are preferably chosen from the group consisting of polar oils, for example from the group consisting of triglycerides or lecithins, and in particular from the group consisting of polar oils of vegetable origin. If the interfacial tension towards water is taken as a measure of the polarity index of an oil or an oil phase, then the polarity of the oil phase concerned is greater the lower the interfacial tension between this oil phase and water. The physical unit of interfacial tension is usually mN/m (millinewtons divided by meters). An arbitrary limit below which an oil phase is regarded as "polar" and above which an oil phase is regarded as "nonpolar" is usually taken to be 30 mN/m.

According to the invention, the oil phase is advantageously, but not necessarily, chosen from the group consisting of polar oil components which have a polarity between 10 and 30 mN/m. It is advantageous to use polar vegetable oils as the main component of the oil phase. The vegetable oils can advantageously be chosen from the group consisting of oils from the plant families Euphorbiaceae, Poaceae, Fabaceae, Brassicaceae, Pedalaceae, Asteraceae, Linaceae, Flacourticaceae, Violales, preferably selected from the group consisting of native castor oil, wheatgerm oil, grapeseed oil, safflower oil, thistle oil and evening primrose oil.

It is very advantageous to choose the oils according to the invention from the group consisting of soybean oil, sunflower oil, wheatgerm oil, castor oil and grapeseed oil.

In addition to the constituents specified above, the compositions according to the invention comprise water and, when required, the additives customary in cosmetics, for example emulsifiers, thickeners, solubilizers, perfume, dyes, deodorants, antimicrobial substances, refatting agents, complexing agents and sequestering agents, pearlizing agents, plant extracts, vitamins, active substances and the like.

The preparations according to the invention optionally also comprise one or more emulsifiers. These are advantageously selected from the group consisting of fatty alcohol ethoxylates of the general formula R—O—(—CH$_2$—CH$_2$—O—)$_n$—H, in which R is a branched or unbranched alkyl, aryl or alkenyl radical, and n is a number from 10 to 50, ethoxylated wool wax alcohols, polyethylene glycol ethers of the general formula R—O—(—CH$_2$—CH$_2$—O—)$_n$—R', in which R and R', independently of one another, are branched or unbranched alkyl or alkenyl radicals, and n is a number from 10 to 80, fatty acid ethoxylates of the general formula R—COO—(—CH$_2$—CH$_2$—O—)$_n$—H, in which R is a branched or unbranched alkyl or alkenyl radical, and n is a number from 10 to 40, etherified fatty acid ethoxylates of the general formula R—COO—(—CH$_2$—CH$_2$—O—)$_n$—R', in which R and R', independently of one another, are branched or unbranched alkyl or alkenyl radicals, and n is a number from 10 to 80, esterified fatty acid ethoxylates of the general formula R—COO—(—CH$_2$—CH$_2$—O—)$_n$—C(O)—R', in which R and R', independently of one another, are branched or unbranched alkyl or alkenyl radicals, and n is a number from 10 to 80, polyethylene glycol glycerol fatty acid esters of saturated and/or unsaturated, branched and/or unbranched fatty acids having a degree of ethoxylation between 3 and 50, ethoxylated sorbitan esters having a degree of ethoxylation of between 3 and 100, cholesterol ethoxylates having a degree of ethoxylation of between 3 and 50, ethoxylated triglycerides having a degree of ethoxylation of between 3 and 150, alkyl ether carboxylic acids of the general formula R—O—(—CH$_2$—CH$_2$—O—)$_n$—CH$_2$—COOH and cosmetically or pharmaceutically acceptable salts thereof, in which R is a branched or unbranched alkyl or alkenyl radical having 5–30 carbon atoms, and n is a number from 5 to 30, polyoxyethylene sorbitol fatty acid esters based on branched or unbranched alkanoic or alkenoic acids and having a degree of ethoxylation of from 5 to 100, for example of the sorbeth type, alkyl ether sulphates and the parent acids of these sulphates of the general formula R—O—(—CH$_2$—CH$_2$—O—)$_n$—SO$_3$—H having cosmetically or pharmaceutically acceptable cations, in which R is a branched or unbranched alkyl or alkenyl radical having 5–30 carbon atoms, and n is a number from 1 to 50, fatty alcohol propoxylates of the general formula R—O—(—CH$_2$—CH(CH$_3$)—O—)$_n$—H, in which R is a branched or unbranched alkyl or alkenyl radical, and n is a number from 10 to 80, polypropylene glycol ethers of the general formula R—O—(—CH$_2$—CH(CH$_3$)—O—)$_n$—R', in which R and R', independently of one another, are branched or unbranched alkyl or alkenyl radicals, and n is a number from 10 to 80, propoxylated wool wax alcohols, etherified fatty acid propoxylates of the general formula R—COO—(—CH$_2$—CH(CH$_3$)—O—)$_n$—R', in which R and R', independently of one another, are branched or unbranched alkyl or alkenyl radicals, and n is a number from 10 to 80, esterified fatty acid propoxylates of the general formula R—COO—(—CH$_2$—CH(CH$_3$)—O—)$_n$—R', in which R and R', independently of one another, are branched or unbranched alkyl or alkenyl radicals, and n is a number from 10 to 80, fatty acid propoxylates of the general formula R—COO—(—CH$_2$—CH(CH$_3$)—O—)$_n$—H, in which R is a branched or unbranched alkyl or alkenyl radical, and n is a number from 10 to 80, polypropylene glycol glycerol fatty acid esters of saturated and/or unsaturated, branched and/or unbranched fatty acids having a degree of propoxylation of between 3 and 80, propoxylated sorbitan esters having a degree of propoxylation of from 3 to 100, cholesterol propoxylates having a degree of propoxylation of from 3 to 100, propoxylated triglycerides having a degree of propoxylation of from 3 to 100, alkyl ether carboxylic acids of the general formula R—O—(—CH$_2$—CH (CH$_3$)O—)$_n$—CH$_2$—COOH and cosmetically or pharmaceutically acceptable salts thereof, in which R is a branched or unbranched alkyl or alkenyl radical, and n is a number from 3 to 50, alkyl ether sulphates and the parent acids of the sulphates of the general formula R—O—(—CH$_2$—CH(CH$_3$)—O—)$_n$—SO$_3$—H having cosmetically or pharmaceutically acceptable cations, in which R is a branched or unbranched alkyl or alkenyl radical having 5–30 carbon atoms, and n is a number from 1 to 50, fatty alcohol ethoxylates/propoxylates of the general formula R—O—X$_n$—Y$_m$—H, in which R is a branched or unbranched alkyl or alkenyl radical, in which X and Y are not identical and are each either an oxyethylene group or an oxypropylene group, and n and m, independently of one another, are numbers from 5 to 50, polypropylene glycol ethers of the general formula R—O—X$_n$—Y$_m$—R', in which R and R', independently of one another, are branched or unbranched alkyl or alkenyl radicals, in which X and Y are not identical and are each either an oxyethylene group or an oxypropylene group, and n and m, independently of one another, are numbers from 5 to 100, etherified fatty acid propoxylates of the general formula R—COO—X$_n$—Y$_m$—R', in which R and R', independently of one another, are branched or unbranched alkyl or alkenyl radical, in which X and Y are not identical and are each either an oxyethylene group or an oxypropylene group, and n and m, independently of one another, are numbers from 5 to 100, fatty acid ethoxylates/propoxylates of the general formula R—COO—X$_n$—Y$_m$—H, in which R is a branched or unbranched alkyl or alkenyl radical, in which X and Y are not identical and are each either an oxyethylene group or an oxypropylene group, and n and m, independently of one another, are numbers from 5 to 50.

In particular, it is advantageous to choose solubilizers from the group consisting of polyoxyethylene-polyoxypropylene block copolymers. Such block copolymers are known under the name "poloxamers" and are characterized by the following structure:

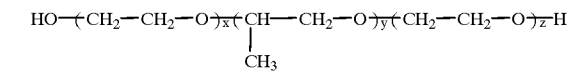

x is advantageously a value between 2 and 20. y is advantageously a value between 10 and 50. z is advantageously a value between 2 and 20.

If, in addition to the surfactants according to the invention, preparations according to the present invention are to contain further surfactants, it is preferable that their concentration is chosen such that it is not greater than 5% by weight, based on the weight of the total composition.

According to the invention, favourable antioxidants are all those which are suitable or customary for cosmetic and/or dermatological applications.

The antioxidants are advantageously selected from the group consisting of amino acids (e.g. glycine, histidine, tyrosine, tryptophan) and derivatives thereof, imidazoles (e.g. urocanic acid) and derivatives thereof, peptides such as D,L-carnosine, D-carnosine, L-carnosine and derivatives thereof (e.g. anserine), carotenoids, carotenes (e.g. α-carotene, β-carotene, lycopene) and derivatives thereof, lipoic acid and derivatives thereof (e.g. dihydrolipoic acid), aurothioglucose, propylthiouracil and other thiols (e.g. thioredoxin, glutathione, cysteine, cystine, cystamine and the glycosyl, N-acetyl, methyl, ethyl, propyl, amyl, butyl and lauryl, palmitoyl, oleyl, gamma-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts) and sulphoximine compounds (e.g. buthioninesulphoximines, homocysteine sulphoximine, buthionine sulphones, penta-, hexa-, heptathionine sulphoximine) in very low tolerated doses (e.g. pmol to µmol/kg), also (metal) chelating agents (e.g. α-hydroxyfatty acids, palmitic acid, phytic acid, lactoferrin), α-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (e.g. gamma-linolenic acid, linoleic acid, oleic acid), folic acid and derivatives thereof, ubiquinone and ubiquinol and derivatives thereof, vitamin C and derivatives (e.g. ascorbyl palmitate, Mg ascorbyl phosphate, ascorbyl acetate), tocopherols and derivatives (e.g. vitamin E acetate), vitamin A and derivatives (vitamin A palmitate) and coniferyl benzoate of benzoin, rutinic acid and derivatives thereof, ferulic acid and derivatives thereof, butylated hydroxytoluene, butylated hydroxyanisole, nordihydroguaiac acid, nordihydroguaiaretic acid, trihydroxybutyrophenone, uric acid and derivatives thereof, mannose and derivatives thereof, zinc and derivatives thereof (e.g. ZnO, ZnSO$_4$ selenium and derivatives thereof (e.g. selenium methionine,), stilbenes and derivatives thereof (e.g. stilbene oxide, trans-stilbene oxide) and the derivatives of these specified active substances which are suitable according to the invention (salts, esters, ethers, sugars, nucleotides, nucleosides, peptides and lipids).

For the purposes of the present invention, oil-soluble antioxidants may be used particularly preferably.

The amount of the antioxidants (one or more compounds) in the preparations is preferably from 0.001 to 30% by weight, particularly preferably 0.05–20% by weight, in particular 1–10% by weight, based on the total weight of the preparation.

If vitamin E and/or derivatives thereof are used as the antioxidant(s), it is advantageous to choose their respective concentrations from the range 0.001–10% by weight, based on the total weight of the formulation.

If vitamin A or vitamin A derivatives, or carotenes or derivatives thereof are used as the antioxidant(s), it is advantageous to choose their respective concentrations from the range 0.001–10% by weight, based on the total weight of the formulation.

The following examples serve to illustrate the present invention, the numerical values in the examples referring to percentages by weight, based on the total weight of the respective preparations.

Example 1

| | |
|---|---|
| TIPA laureth sulphate | 36 |
| Castor oil | 30 |
| PEG-40 sorbitan peroleate | 15 |
| Cocamide DEA | 10 |
| Propylene glycol | 9 |

Example 2

| | |
|---|---|
| TIPA laureth sulphate | 34 |
| Castor oil | 30 |
| PEG-40 sorbitan peroleate | 15 |
| Cocamide DEA | 10 |
| Soybean oil | 9 |
| Propylene glycol | 2 |

Example 3

| | |
|---|---|
| TIPA laureth sulphate | 34 |
| Castor oil | 30 |
| Cocamide DEA | 10 |
| PEG-40 sorbitan perisostearate | 10 |
| Soybean oil | 9 |
| Propylene glycol | 2 |
| Water | 1 |
| Perfume, antioxidants, preservatives | q.s. |

Example 4

| | |
|---|---|
| TIPA laureth sulphate | 34 |
| Castor oil | 30 |
| Soybean oil | 15 |
| Cocamide DEA | 10 |
| PEG-40 sorbitan perisostearate | 5 |
| Propylene glycol | 2 |
| Water | 1.8 |
| Perfume, antioxidants, preservatives | q.s. |

Example 5

| | |
|---|---|
| TIPA laureth sulphate | 36 |
| Castor oil | 30 |
| PEG-40 sorbitan peroleate | 10 |
| Cocamide DEA | 10 |
| Propylene glycol | 9 |
| Grapeseed oil | 5 |

What is claimed is:

1. Cosmetic or dermatological shower preparations comprising (a) a content of at most 55% by weight, based on the total weight of the preparations, of one or more surfactants selected from the group consisting of trialkyl- and/or trialkanolamine salts of fatty alcohol ether sulphates of the formula:

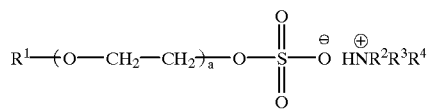

wherein a is from 1 to 10, and $R^1$ is selected from the group consisting of branched and unbranched alkyl groups having from 6 to 24 carbon atoms, and $R^2$, $R^3$ and $R^4$ independently are selected from the group consisting of branched and unbranched alkyl and hydroxyalkyl radicals having from 1 to 24 carbon atoms, (b) a content of from 30 to 45% by weight, based on the total weight of the preparations, of one or more oil components selected from the group consisting of lipids, which contain from one to three acyl radicals, which have been esterified using an alcohol;

(c) a content of at most 3.5% by weight, based on the total weight of the preparation, of water, (d) optionally one or more emulsifiers, (e) optionally further surfactants, and (f) optionally further cosmetic or pharmaceutical auxiliaries, additives or active substances.

2. Shower preparations according to claim 1, wherein the alcohol which is used to carry out the esterification is glycerol, glycerol 3-phosphate and/or sphingosine.

3. Shower preparations according to claim 1, wherein the oil components are selected from the group consisting of oils having a high content of triglycerides of saturated or unsaturated, branched and/or unbranched fatty acids or from the group consisting of lecithins.

4. Shower preparations according to claim 1, wherein $R^2$, $R^3$ and $R^4$ have the following structure:

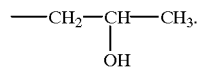

5. Shower preparations according to claim 1, wherein the oils are selected from the group consisting of polar oils which have a polarity between 10 and 30 mN/m.

6. Shower preparations according to claim 1, wherein the oils are selected from the group consisting of triglycerides of the following structure:

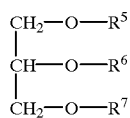

in which $R^5$, $R^6$ and $R^7$, independently of one another, are selected from the group consisting of branched and unbranched, alkylcarboxyl and alkenylcarboxyl groups having from 12 to 24 carbon atoms, wherein one or more aliphatic hydrogen atoms in the alkylcarboxyl and alkenylcarboxyl groups are optionally substituted by hydroxyl groups.

7. Shower preparations according to claim 7, wherein $R^5$, $R^6$ and/or $R^7$ contain from 16 to 20 carbon atoms and are selected from the group consisting of mono- to triunsaturated carboxylic acid radicals.

8. Shower preparations according to claim 1, wherein the oil or oils are selected from the group consisting of soybean oil, sunflower oil, wheatgerm oil, castor oil and grapeseed oil.

9. Shower preparations according to claim 1, wherein a is from 1 to 5.

10. A method of cleansing skin comprising applying thereto a cosmetic or dermatologic shower preparation according to any one of claims 1–3 or 5–9.

* * * * *